(12) United States Patent
Yang et al.

(10) Patent No.: US 8,859,455 B2
(45) Date of Patent: Oct. 14, 2014

(54) NANOCRYSTAL ASSEMBLY FOR TANDEM CATALYSIS

(75) Inventors: Peidong Yang, Kensington, CA (US); Gabor Somorjai, Berkeley, CA (US); Yusuke Yamada, Osaka (JP); Chia-Kuang Tsung, Allston, MA (US); Wenyu Huang, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 63 days.

(21) Appl. No.: 13/441,240

(22) Filed: Apr. 6, 2012

(65) Prior Publication Data

US 2012/0302437 A1   Nov. 29, 2012

Related U.S. Application Data

(60) Provisional application No. 61/473,451, filed on Apr. 8, 2011.

(51) Int. Cl.
| | | |
|---|---|---|
| *B01J 21/00* | (2006.01) | |
| *B01J 23/00* | (2006.01) | |
| *B01J 23/63* | (2006.01) | |
| *B01J 23/42* | (2006.01) | |
| *B01J 37/02* | (2006.01) | |
| *C01B 3/22* | (2006.01) | |
| *B01J 35/00* | (2006.01) | |
| *C07C 45/49* | (2006.01) | |

(52) U.S. Cl.
CPC ........... *B01J 23/63* (2013.01); *C01B 2203/107* (2013.01); *C01B 2203/1223* (2013.01); *B01J 23/42* (2013.01); *B01J 37/0244* (2013.01); *C01B 2203/1082* (2013.01); *C01B 3/22* (2013.01); *B01J 35/0013* (2013.01); *C01B 2203/0277* (2013.01); *C07C 45/49* (2013.01)
USPC .......................................... 502/262; 502/300

(58) Field of Classification Search
None
See application file for complete search history.

(56) References Cited

PUBLICATIONS

Yamada et al (Nanocrystal bilayer for tandem catalysis, Nature Chem, (2011), 3, pp. 372-376).*
Ma et al (Surface Modification of Au/TiO2 Catalysts by SiO2 via Atomic Layer Deposition, J Phys Chem, 2008, 112(25), pp. 9448-9457).*
Wasilke, J. C. et al. Concurrent tandem catalysis. Chem. Rev. 105, 1001-1020 (2005).
Ott, L. S. & Finke, R. G. Transition-metal nanocluster stabilization for catalysis: a critical review of ranking methods and putative stabilizers. Coord. Chem. Rev. 251, 1075-1100 (2007).
Somorjai, G. A., Frei, H. & Park, J. Y. Advancing the frontiers in nanocatalysis, biointerfaces, and renewable energy conversion by innovations of surface techniques. J. Am. Chem. Soc. 131, 16589-16605 (2009).

(Continued)

*Primary Examiner* — Melvin C Mayes
*Assistant Examiner* — Michael Forrest
(74) *Attorney, Agent, or Firm* — Lawrence Berkeley National Laboratory (57) ABSTRACT

The present invention provides a nanocrystal tandem catalyst comprising at least two metal-metal oxide interfaces for the catalysis of sequential reactions. One embodiment utilizes a nanocrystal bilayer structure formed by assembling sub-10 nm platinum and cerium oxide nanocube monolayers on a silica substrate. The two distinct metal-metal oxide interfaces, $CeO_2$—Pt and Pt—$SiO_2$, can be used to catalyze two distinct sequential reactions. The $CeO_2$—Pt interface catalyzed methanol decomposition to produce CO and $H_2$, which were then subsequently used for ethylene hydroformylation catalyzed by the nearby Pt—$SiO_2$ interface. Consequently, propanal was selectively produced on this nanocrystal bilayer tandem catalyst.

14 Claims, 10 Drawing Sheets

(56) References Cited

PUBLICATIONS

Somorjai, G. A., Tao, F. & Park, J. Y. The nanoscience revolution: merging of colloid science, catalysis and nanoelectronics. Top. Catal. 47, 1-14 (2008).

Si, R. & Flytzani-Stephanopoulos, M. Shape and crystal-plane effects of nanoscale ceria on the activity of Au-CeO2 catalysts for the water—gas shift reaction. Angew. Chem. Int. Ed. 47, 2884-2887 (2008).

Xie, X. W., Li, Y., Liu, Z. Q., Haruta, M. & Shen, W. J. Low-temperature oxidation of CO catalysed by Co3O4 nanorods. Nature 458, 746-749 (2009).

Stakheev, A. Y. & Kustov, L. M. Effects of the support on the morphology and electronic properties of supported metal clusters: modern concepts and progress in 1990s. Appl. Catal. A 188, 3-35 (1999).

Jackson, S. D. et al. Supported metal catalysts: preparation, characterization, and function. 5. Activities and selectivities of platinum catalysts in the reactions of cyclopropane, ethene, 1,3-butadiene, and 2-butyne with dihydrogen. J. Catal. 162, 10-19 (1996).

Jackson, S. D., Kelly, G. J. & Webb, G. Supported metal catalysts; preparation, characterisation, and function—Part VI. Hydrogenolysis of ethane, propane, n-butane and iso-butane over supported platinum catalysts. J. Catal. 176, 225-234 (1998).

Zhou, Z., Kooi, S., Flytzani-Stephanopoulos, M. & Saltsburg, H. The role of the interface in CO oxidation on Au/CeO2 multi-layer nanotowers. Adv. Funct. Mater. 18, 2801-2807 (2008).

Shevchenko, E. V., Talapin, D. V., Kotov, N. A., O'Brien, S. & Murray, C. B. Structural diversity in binary nanoparticle superlattices. Nature 439, 55-59 (2006).

Urban, J. J., Talapin, D. V., Shevchenko, E. V., Kagan, C. R. & Murray, C. B. Synergism in binary nanocrystal superlattices leads to enhanced p-type conductivity in self-assembled PbTelAg2Te thin films. Nat. Mater. 6,115-121 (2007).

Croy, J. R. et al. Support dependence of MeOH decomposition over size-selected Pt nanoparticles. Catal. Lett. 119, 209-216 (2007).

Imamura, S. et al. Decomposition of methanol on Pt-loaded ceria. Catal. Today 50,369-380 (1999).

Centi, G. & Perathoner, S. Catalysis: role and challenges for a sustainable energy. Top. Catal. 52,948-961 (2009).

Norskov, J. K., Bligaard, T., Rossmeisl, J. & Christensen, C. H. Towards the computational design of solid catalysts. Nat. Chem. 1,37-46 (2009).

Aliaga, C. et al. Sum frequency generation and catalytic reaction studies of the removal of organic capping agents from Pt nanoparticles by UV-ozone treatment. J. Phys. Chem. C 113,6150-6155 (2009).

Lee, H. et al. Morphological control of catalytically active platinum nanocrystals. Angew. Chem. Int. Ed. 45,7824-7828 (2006).

Yang, S. & Gao, L. Controlled synthesis and self-assembly of CeO2 nanocubes. J. Am. Chem. Soc. 128,9330-9331 (2006).

Contreras, A. M., Yan, X.-M., Kwon, S., Bokor, J. & Somorjai, G. A. Catalytic CO oxidation reaction studies on lithographically fabricated platinum nanowire arrays with different oxide supports. Catal. Lett. 111,5-13 (2006).

Kweskin, S. J. et al. Carbon monoxide adsorption and oxidation on monolayer films of cubic platinum nanoparticles investigated by infrared—visible sum frequency generation vibrational spectroscopy. J. Phys. Chem. B 110,15920-15925 (2006).

Panagiotopoulou, P. & Kondarides, D. I. A comparative study of the water—gas shift activity of Pt catalysts supported on single (MOx) and composite (MOx/A12O3, M0x/TiO2) metal oxide carriers. Catal. Today 127,319-329 (2007).

* cited by examiner

NANOCRYSTAL ASSEMBLY FOR TANDEM CATALYSIS

CROSS REFERENCE TO RELATED CASE

This U.S. application claims priority to U.S. Provisional Application Ser. No. 61/473,451 filed Apr. 8, 2011, which application is incorporated herein by reference as if fully set forth in their entirety.

STATEMENT OF GOVERNMENT SUPPORT

This invention was made with government support under Contract No. DE-AC02-05CH11231 awarded by the U.S. Department of Energy to the Regents of the University of California for the operation and management of the Lawrence Berkeley National Laboratory. The government has certain rights in this invention.

FIELD OF INVENTION

The present invention relates to the field of catalysts, and particularly relates to a nanocrystal assembly for tandem catalysis.

BACKGROUND OF THE INVENTION

Supported catalysts have been widely used in industries because of easy handling and robustness, however, their catalysis improvement appears incrementle. High performance catalysts are central for the development of new generation energy conversion and storage technologies.[1,2] While industrial catalysts can be optimized empirically by tuning the elemental composition, changing the supports, or altering preparation conditions in order to achieve higher activity and selectivity, these conventional catalysts are typically not uniform in composition and/or surface structure at the nano- to micro-scale. In order to significantly improve our capability of designing better catalysts, new concepts for the rational design and assembly of metal-metal oxide interfaces are desired. Rational design of metal-metal oxide interfaces in nanostructured catalysts is critical for achieving better reaction activities and selectivities.

BRIEF DESCRIPTION OF THE DRAWINGS

The present invention is described with respect to particular exemplary embodiments thereof and reference is accordingly made to the drawings in which.

DETAILED DESCRIPTION OF THE INVENTION

Metal nanocrystals with well-controlled shape and size are interesting materials for catalyst design from both electronic structure and surface structure aspects.[3,4,5] From the electronic structure point of view, small metal nanoclusters have size-dependent electronic states, which make them fundamentally different from the bulk material. From the surface structure point of view, the shaped nanocrystals have surfaces with well-defined atomic arrangements. It has been clearly demonstrated by surface science studies in recent decades that the atomic arrangement on the crystal surface can affect catalytic phenomena in terms of activity, selectivity, and durability.

The application of shape- and size-controlled metal oxide nanocrystals as catalyst supports has even greater potential for innovative catalyst design.[6,7] It is known that catalysis can be modulated by using different metal oxide supports, or metal oxide supports with different crystal surfaces.[8] For example, platinum loaded molybdenum oxide and silica catalysts, have both shown similar activation energies for ethylene hydrogenation.[9] On the other hand, the activation energy for ethane hydrogenolysis over platinum-silica was lower than that over platinum-molybdenum oxide.[10] It is believed that the metal oxides not only work as supports, but also function as electronic modulators, in addition to contributing spillover and adsorption sites. The precise selection and control of metal-oxide interfaces could lead to better activity and selectivity for a desired reaction.[11]

Various embodiments of the invention introduce a new class of nanocrystal tandem catalysts having multiple metal-metal oxide interfaces for the catalysis of sequential reactions. One embodiment utilizes a nanocrystal bilayer structure formed by assembling sub-10 nm platinum and cerium oxide nanocube monolayers on a silica substrate. The two distinct metal-metal oxide interfaces, $CeO_2$—Pt and Pt—$SiO_2$, can be used to catalyze two distinct sequential reactions. The $CeO_2$—Pt interface catalyzed methanol decomposition to produce CO and $H_2$, which were then subsequently used for ethylene hydroformylation catalyzed by the nearby Pt—$SiO_2$ interface. Consequently, propanal was selectively produced on this nanocrystal bilayer tandem catalyst. This new concept of nanocrystal tandem catalysis represents a powerful approach towards designing high performance, multi-functional nanostructured catalysts.

The integration of multiple types of metal-metal oxide interfaces on the surface of a single active metal nanocrystal could in principle yield a novel tandem catalyst for multi-step reactions. The catalytic activity and selectivity of such a tandem catalyst can be optimized by establishing suitable metal oxide interfaces for each reaction step. However, it is difficult to control the composition of multiple interfaces on an atomic level using traditional catalyst synthesis. Integrating binary nanocrystals to form highly ordered superlattice represents a new way to form multiple interfaces with new functionalities.[12,13] An embodiment of the invention utilizes a nanocrystal bilayer structure formed by assembling sub-10 nm platinum and cerium oxide nanocube monolayers on a silica substrate. The two distinct metal-metal oxide interfaces in the catalyst, $CeO_2$—Pt and Pt—$SiO_2$, were used to catalyze two separate and sequential reactions. The $CeO_2$—Pt interface catalyzed methanol decomposition to produce CO and $H_2$ which were subsequently used for ethylene hydroformylation catalyzed by the nearby Pt—$SiO_2$ interface. Consequently, propanal was selectively produced on this nanocrystal bilayer tandem catalyst.

Figure 1:
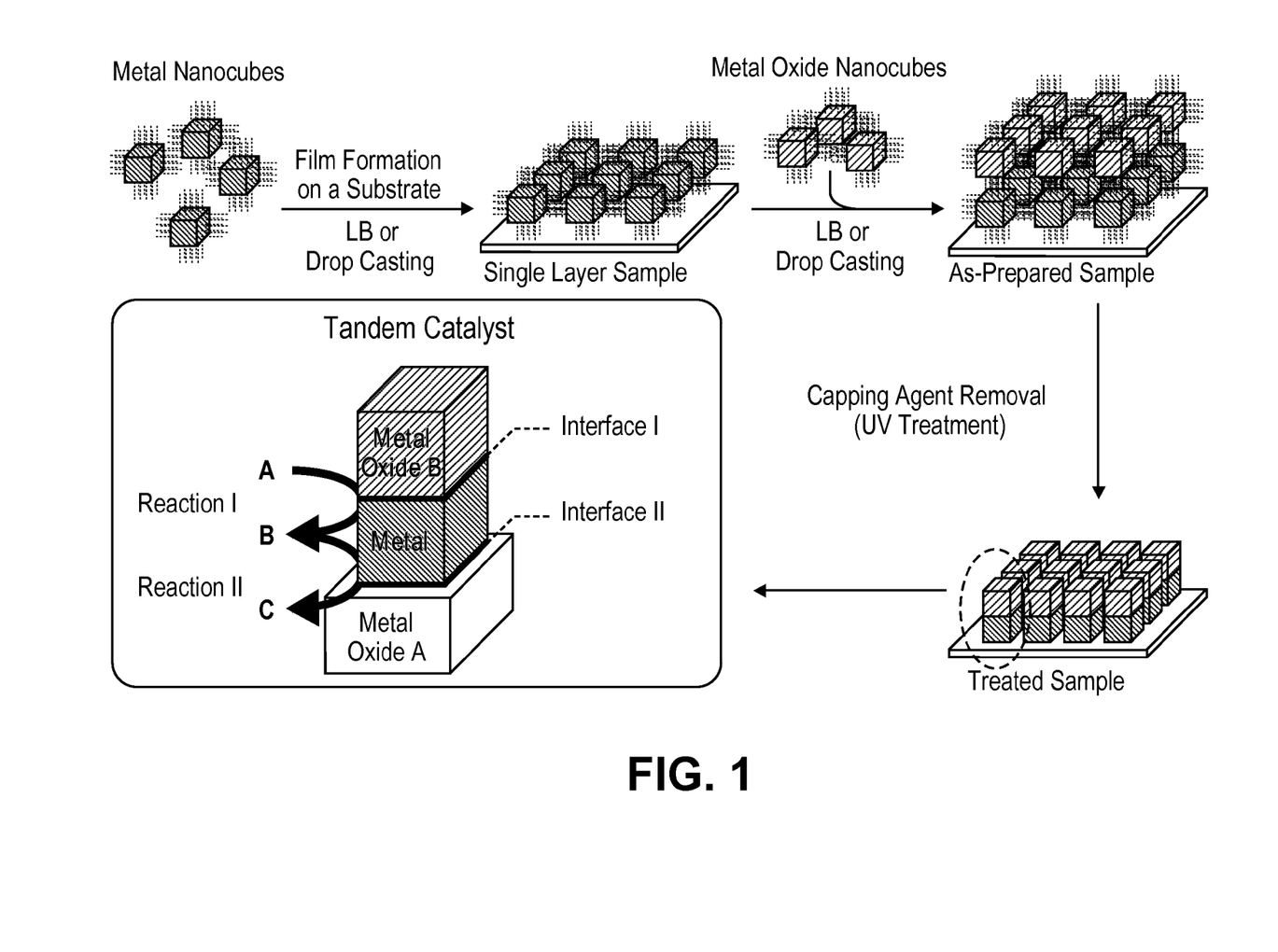
FIG. 1 illustrates the assembly process for the preparation of nanocrystal bilayer "tandem catalyst".

The cubic shape of nanocrystals is ideal for assembling metal-metal oxide interfaces with a large contact area. FIG. 1 shows a method to achieve the "tandem" bilayer structure with nanocubes of metal and metal oxide. First, a two dimensional metal (Pt) nanocube array was assembled onto flat metal oxide substrate ($SiO_2$) by using the Langmuir-Blodgett (LB) method to make the first metal-metal oxide interface. The second metal oxide ($CeO_2$) nanocube LB array was then assembled on top of the metal nanocube monolayer, which provides the second metal-metal oxide interface. The capping agents of the nanocrystals were removed by UV/ozone treatment to form clean metal-metal oxide interfaces.[20] After the capping agent removal, the vertical clefts between the nanocrystals assure access to both catalytic interfaces, while providing high surface area in the close packed array.

Olefin hydroformylation is an important reaction for the production of aldehydes from olefins, carbon monoxide, and hydrogen.[14] Usually the reaction is carried out with homogeneous catalysts, such as Rh complexes. The disadvantages of this process include the use of toxic CO and explosive $H_2$ gas. This process would also typically employ high pressure conditions and purification processes. Therefore, it would be advantageous to carry out olefin hydroformylation via heterogeneous catalysis with CO and $H_2$ produced in situ from the decomposition of a benign chemical, such as methanol. It is known that Pt loaded on $CeO_2$ shows high activity toward methanol decomposition to provide CO and $H_2$.[15,16] In addition, Naito and Tanimoto reported that Pt loaded $SiO_2$ catalyzed propene hydroformylation and produced aldehydes with a high conversion rate. However, the selectivity for this reaction was poor.[17] Here, an embodiment of the invention demonstrates that nanocrystal bilayer, made of a $CeO_2$ nanocube monolayer and Pt nanocube monolayer on a $SiO_2$ substrate, effectively catalyzes ethylene hydroformylation with methanol to produce propanal selectively.

Results and Discussions

Figure 2:
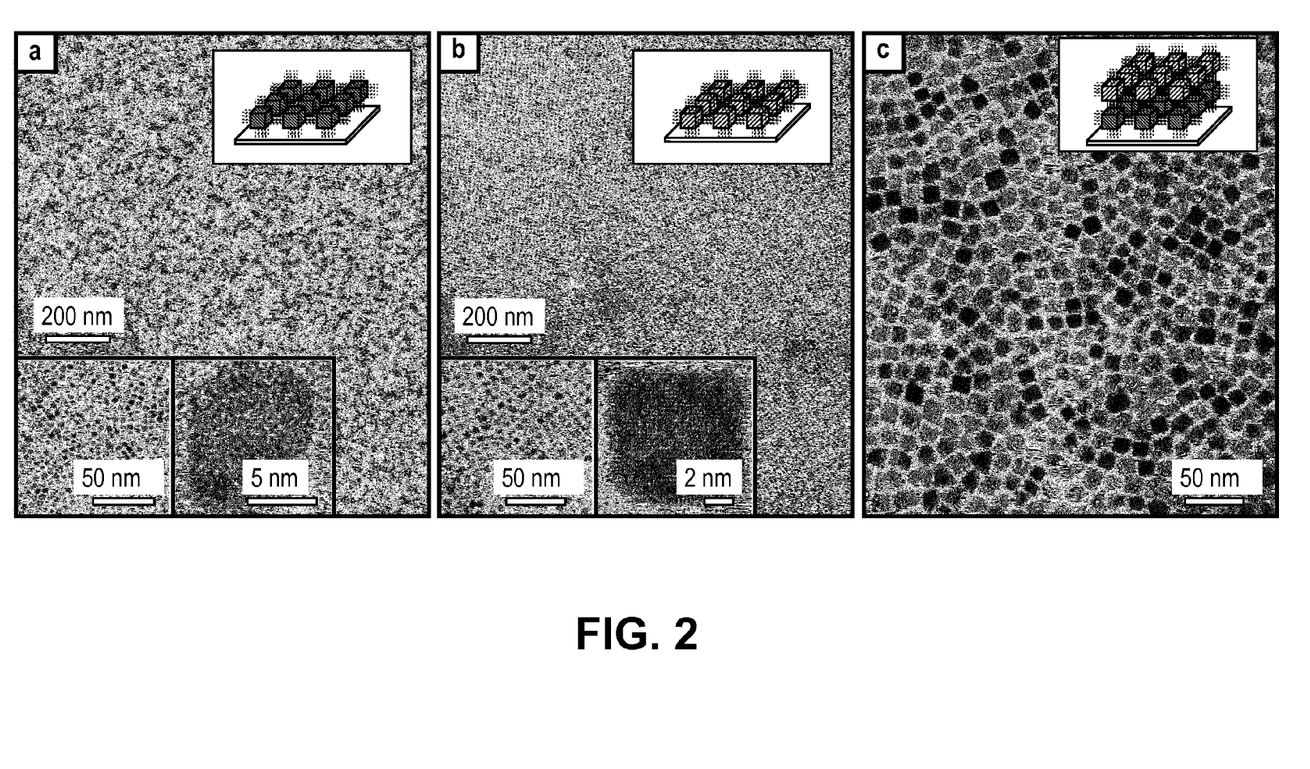
FIG. 2 illustrates monolayer films of Pt nanocubes, $CeO_2$ nanocubes and $CeO_2$—Pt double layer observed by TEM.
Figure 3:
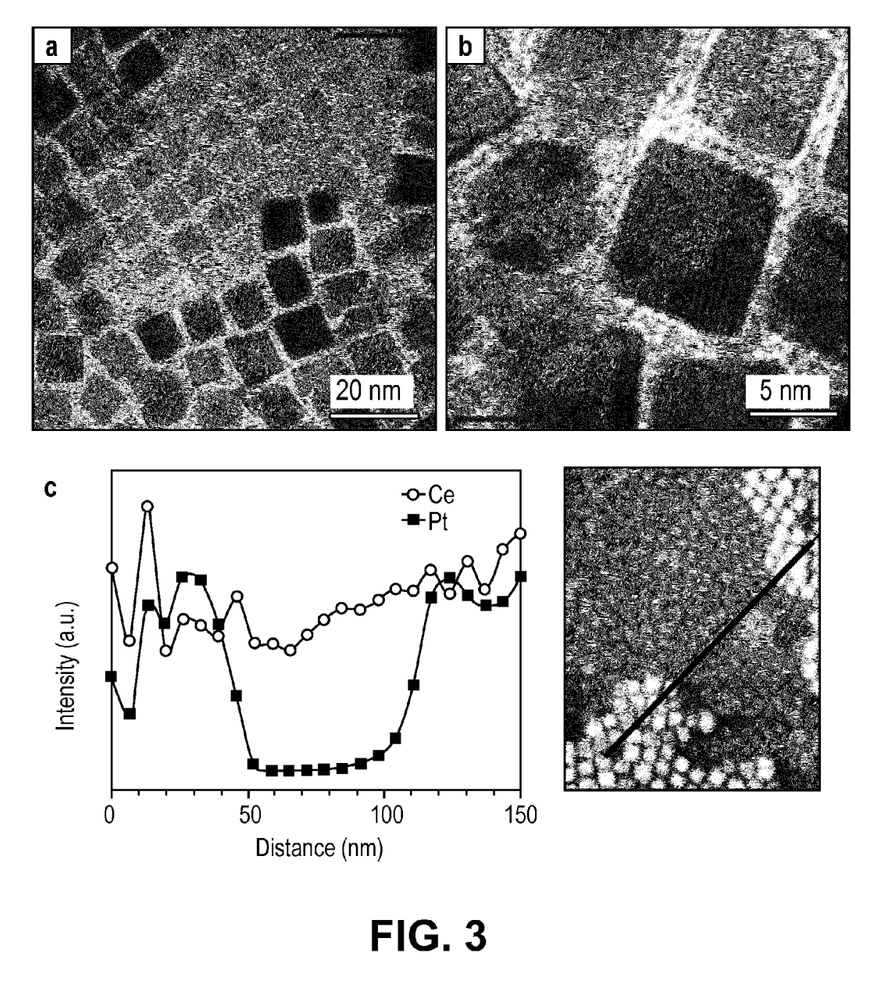
FIG. 3 illustrates nanocrystal bilayers observed by HR TEM and EDX.

Preparation of tandem catalyst Platinum and ceria nanocubes with edge lengths of 6-8 nm were prepared by literature methods with minor modifications.[18,19] A monolayer of platinum nanocubes was prepared by LB, and then transferred onto a Si wafer substrate with a native oxide layer on the surface. The original capping agent on the platinum nanocubes, tetradecyltrimethylammonium bromide (TTAB), was exchanged for oleylamine to facilitate LB assembly and deposition. The high resolution transmission electron microscopy (HRTEM) image of a single Pt nanocube and low magnification TEM images of a Pt LB film are shown in FIG. 2a. The Pt nanocubes are single crystalline and enclosed by six (100) facets. The domain size of the monolayer film is over one micron by one micron, and the total coverage of the film was more than 80%. The gaps between the nanocrystals were about 2-3 nm, which are sufficient for diffusion of small molecules. The oleic acid capped $CeO_2$ nanocube monolayer film was prepared by drop casting or LB. FIG. 2b shows a film prepared by drop casting. The gaps between the nanocrystals are 4-5 nm, which is close to the thickness of the oleic acid bilayer. The dropcast $CeO_2$ film showed long range ordering. For catalytic samples, the $CeO_2$ film was prepared by LB to give a large film area. The double-layered film was obtained by depositing a $CeO_2$ film onto a Pt film. A TEM image of a large area bilayered film of $CeO_2$ on Pt is shown in FIG. 2c. Although the $CeO_2$ nanocrystals above the Pt nanocrystals cannot be clearly observed over most of the area due to their lower contrast, the $CeO_2$ nanocrystals were visible at some defect areas on the Pt film (see FIG. 3a). The presence of $CeO_2$ nanocubes on the Pt nanocube film was confirmed by HRTEM and by performing an energy dispersive X-ray (EDX) spectroscopy line scan as shown in FIGS. 3b and c. The Pt and $CeO_2$ lattice were both observed on the bilayer film by HRTEM (FIG. 3b). The EDX line scan over the defect area of the bilayer film is shown in FIG. 3c. It shows the intensity change of Pt and Ce along the line on the film where the Pt film is discontinuous. The Pt intensity decreases at the gap between Pt nanocrystals while the Ce intensity was nearly constant.

Figure 6:
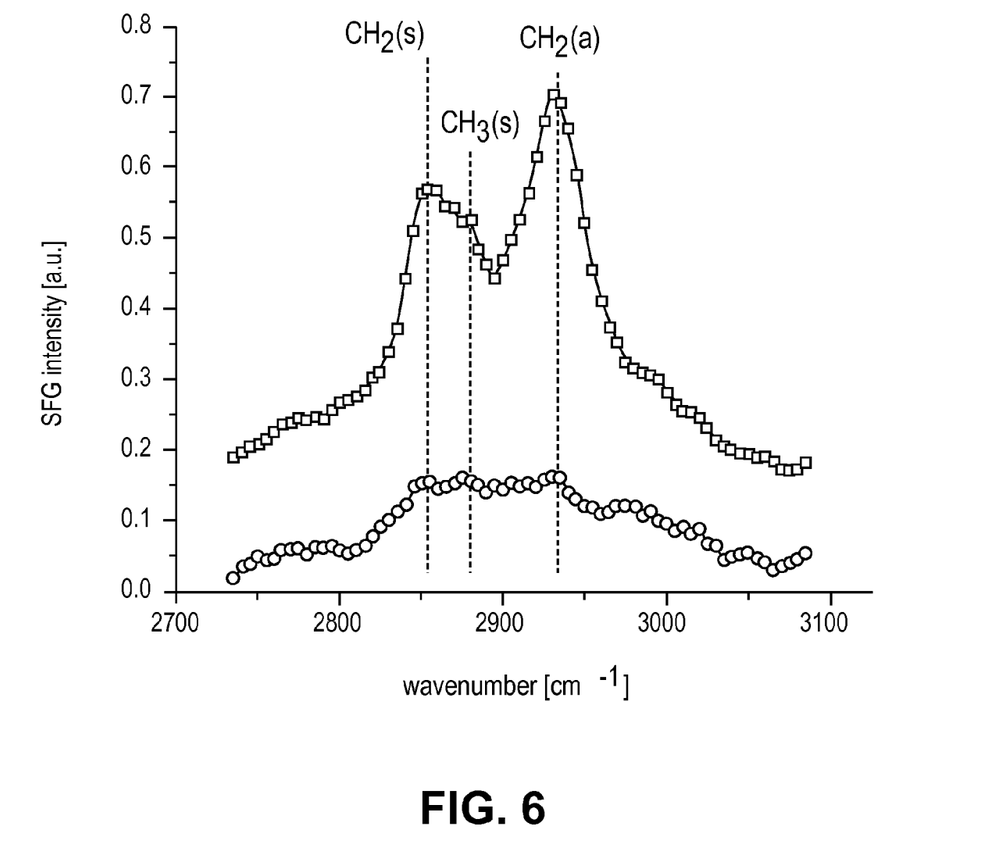
FIG. 6 illustrates sum frequency generation spectra of an LB film of oleylamine-coated Pt nanoparticles after UV/ozone treatment for 200 min.
Figure 7:
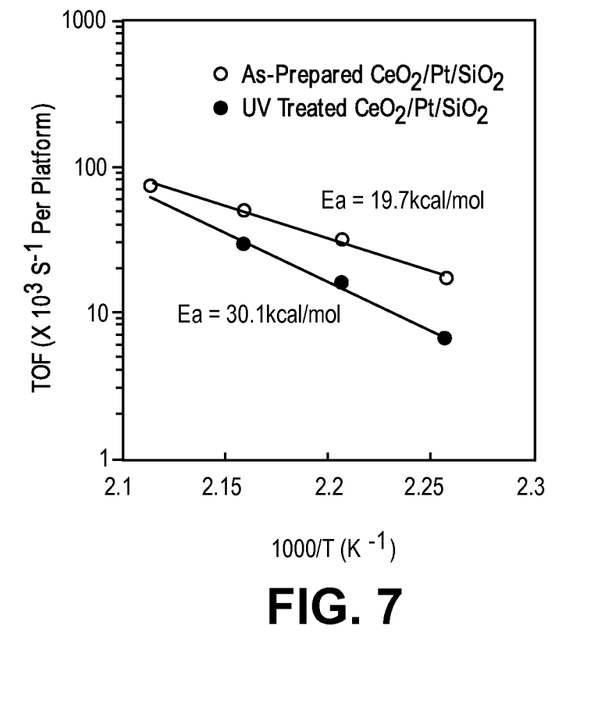
FIG. 7 illustrates turn-over frequency on CO oxidation over $CeO_2$ on Pt nanoparticles.

In order to facilitate interface formation between the $SiO_2$, Pt, and $CeO_2$ layers, the various capping agents, oleylamine on Pt and oleic acid on $CeO_2$, need to be removed. Although $CeO_2$ crystals are stable under high temperature treatment for capping agent removal, Pt nanocubes are not stable under such conditions. When Pt nanocrystal loaded samples were heated at 250° C. in air, the shape of the Pt nanocrystals was lost. Thus, an embodiment applied a room temperature UV-irradiation process to remove surface capping agents. Previously, it was found that UV/ozone treatment is effective for removing organic capping agents from Pt nanoparticles. Here, removal of the capping agent was monitored by sum frequency generation vibrational spectroscopy as shown in FIG. 6. Before the UV/ozone treatment, three peaks assigned to symmetric $CH_2$ (2853 $cm^{-1}$), symmetric $CH_3$ (2879 $cm^{-1}$), and asymmetric $CH_2$ (2929 $cm^{-1}$) stretches, were observed. After treatment, the intensity of the peaks was significantly decreased. TEM observations of the sample before and after the UV/ozone treatment indicated that the crystal shapes remained unchanged. Oxidation of CO is commonly employed to examine the interaction between Pt and metal oxides because the activation energy of Pt loaded on a metal oxide is highly dependent on the nature of metal oxide support.[21,22,23] The strong Pt-metal oxide interaction decreases electron donation from Pt to adsorbed CO weakening the CO bond. As the result, the interaction between Pt and the metal oxide increases the activation energy for CO oxidation. Arrhenius plots for CO oxidation over the $CeO_2$—Pt bilayers on $SiO_2$ substrates before and after UV/ozone treatment are shown in FIG. 7. The as-prepared bilayers showed an apparent activation energy of 19.7 kcal/mol which is comparable to the reported value of Pt nanocubes.[22] The UV/ozone treated samples showed an apparent activation energy of 30.1 kcal/mol. The increase in activation energy indicates the formation of two metal-metal oxide interfaces of $CeO_2$—Pt and Pt—$SiO_2$ following capping agent removal.

Ethylene Hydroformylation Over Tandem Catalyst with Methanol (MeOH).

Figure 4A:
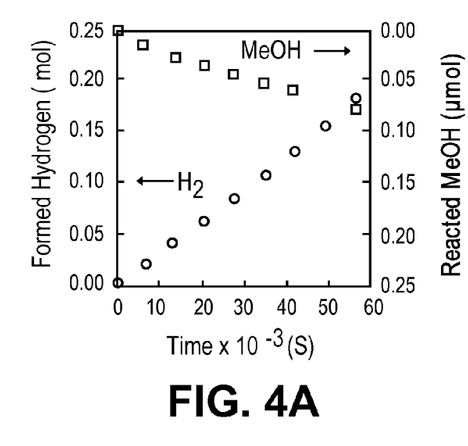
FIG. 4 illustrates MeOH decomposition over Pt/$CeO_2$ and conventional hydroformylation over Pt/$SIO_2$.

The assembly of $CeO_2$—Pt—$SiO_2$, bilayers with two different metal-metal oxide interfaces is an ideal catalyst design for olefin hydroformylation with CO and H-12 formed in situ by the decomposition of methanol (MeOH). It was reported previously that Pt/$CeO_2$ can selectively catalyze MeOH decomposition to CO and $H_2$, while $Pt/SiO_2$ catalyzes olefin hydroformylation. Prior to examining the two-step tandem reaction, control experiments were performed to monitor each step over each interface individually: MeOH decomposition over the $Pt/CeO_2$ interface, and then separately ethylene hydroformylation with CO and $H_2$ gas input over the $Pt/SiO_2$ interface. The decomposition of MeOH over the $Pt/CeO_2$ interface was examined at 190° C. over $Pt$—$CeO_2$—$SiO_2$ catalyst, which contains only of $Pt/CeO_2$—metal/oxide interface. The as-prepared catalyst showed no catalytic activity for the reaction due to the lack of clean metal-metal oxide interfaces (see FIG. 8). After UV/ozone treatment, the $Pt$—$CeO_2$—$SiO_2$ tandem catalyst showed MeOH decomposition activity as shown in FIG. 4a. The concentration of formed hydrogen and decomposed MeOH in the batch reactor changed in proportion to the reaction time and the ratio of formed $H_2$ to decomposed MeOH is 1:2, which confirms the formation of $H_2$ and CO. The turn over frequency, TOF, in terms $H_2$ was $1.8 \times 10^{-3}$ $s^{-1}$ per Pt atom.

Figure 4B:
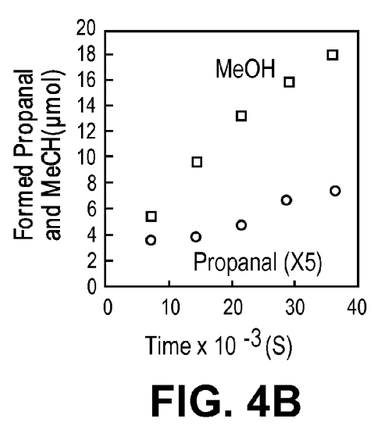
Figure 9:
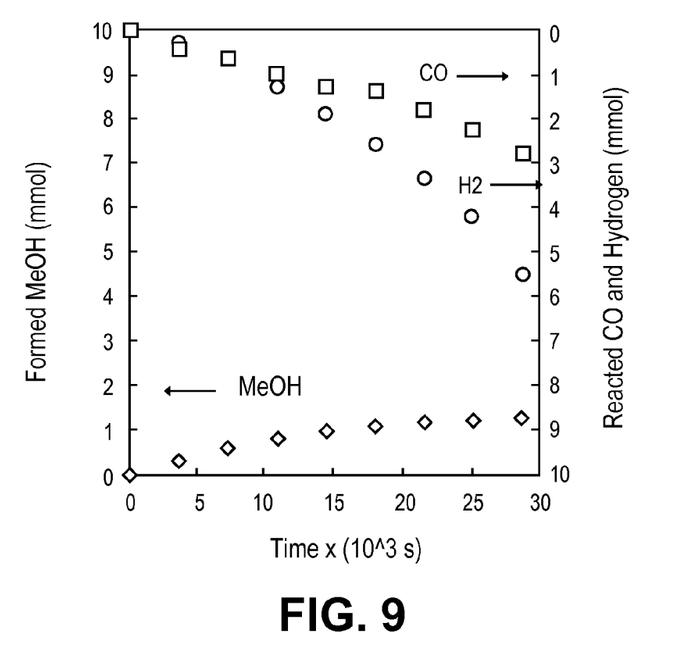
FIG. 9 illustrates CO hydrogenation with CO and $H_2$ (without ethylene) as a function of reaction time over the Pt nanocubes on $SiO_2$.

Separately, ethylene hydroformylation with CO and $H_2$ gas was carried out over the $Pt$—$SiO_2$ catalyst also at 190° C. FIG. 4b shows the concentration change of propanal and MeOH in a batch rector as a function of the reaction time. The propanal formation was clearly observed. The production of MeOH was due to the hydrogenation of CO, which was confirmed by CO hydrogenation with only CO and $H_2$ without ethylene (see FIG. 9). The TOF in terms of MeOH was $5.8 \times 10^{-2}$ $s^{-1}$ per Pt atom and the TOF in terms of propanal was $2.7 \times 10^{-3}$ $s^{-1}$ per Pt atom. On a bare Pt surface, the formation of MeOH by CO hydrogenation is much faster than propanal formation by hydroformylation.

Figure 5A:
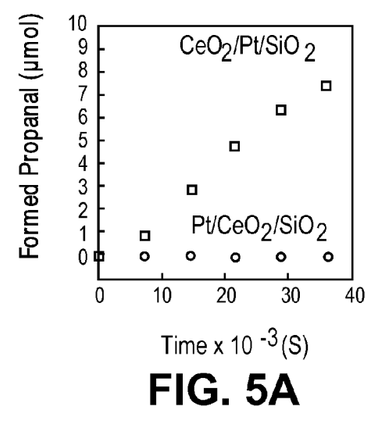
FIG. 5 illustrates ethylene hydroformylation with MeOH over tandem catalyst.
Figure 5B:
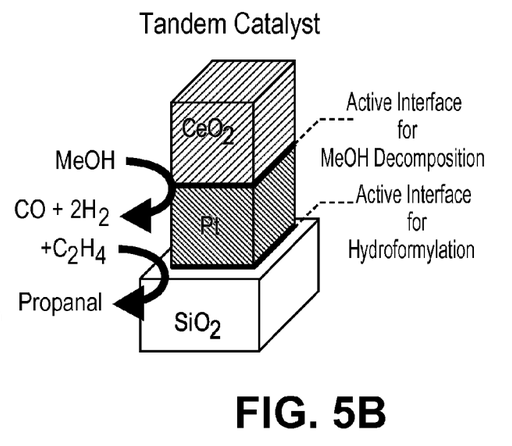
Figure 8A:
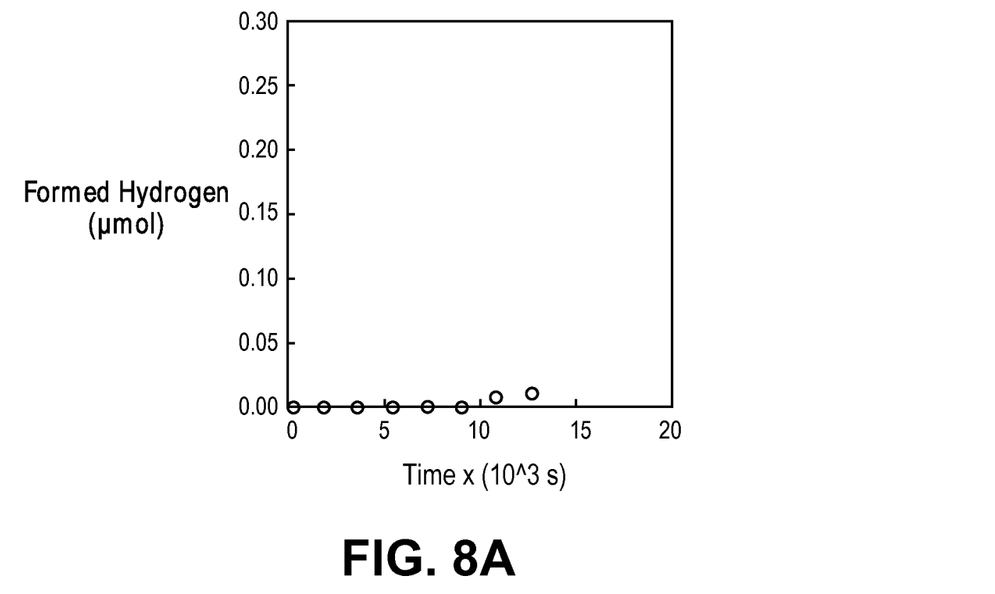
FIG. 8 illustrates the as-prepared catalyst showed no catalytic activity for the reactions due to the lack of clean metal-metal oxide interfaces. (a) Hydrogen produced as a function of reaction time over Pt/$CeO_2$ interface without UV treatment at 190° C. by catalytic thermal decomposition of methanol. (b) Propanal produced as a function of reaction time over $CeO_2$—Pt—$SiO_2$ without UV treatment at 190° C. from ethylene and MeOH.
Figure 8B:
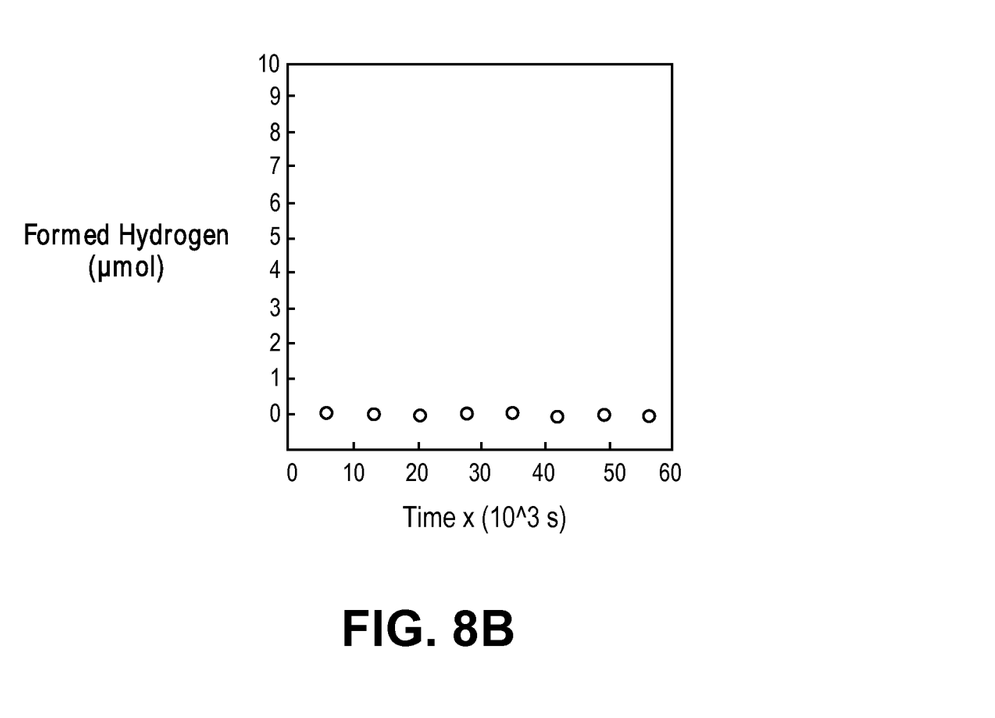
Figure 10:
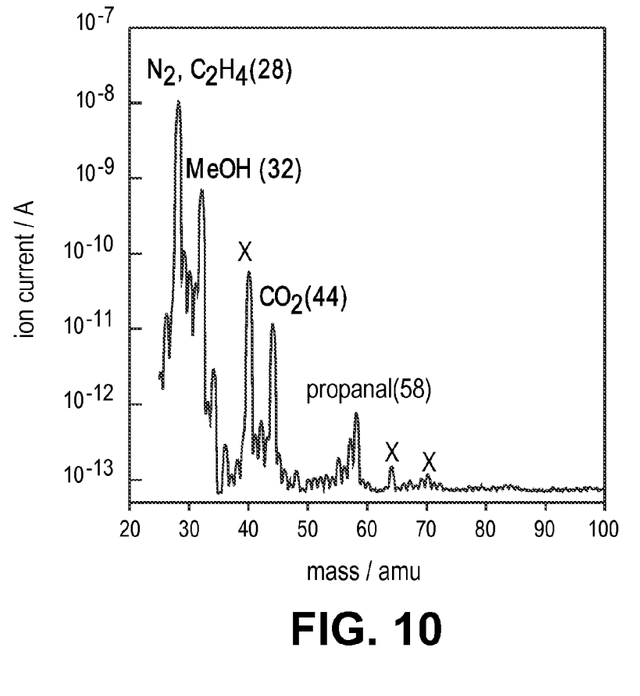
FIG. 10 illustrates a mass spectrogram of the outlet gas after 24 hours reaction.

FIG. 5a shows time dependent propanal formation from ethylene hydroformylation with in situ MeOH decomposition over the $CeO_2$—$Pt$—$SiO_2$ tandem catalyst at 190° C. The as-prepared sample produced a negligible amount of propanal even after a longer reaction time (FIG. 8). On the other hand, the formation of propanal was clearly observed over the UV/ozone treated catalyst as shown in FIG. 5a. Propanal formation over the UV/ozone treated catalyst was further confirmed by a mass spectroscopy and quantified by gas chromatography (see FIG. 10). The formation of by-products such as propanol or ethane was less than the detection limit (<0.01 vol %). The maximum propanal concentration in the reaction effluent was 0.18% where the product selectivity toward propanal was more than 94%. This is quite surprising since simple ethylene hydrogenation, a competitive reaction of hydroformylation, is much faster on conventional Pt catalysts. The same reaction over the $Pt$—$CeO_2$—$SiO_2$ catalyst, which doesn't contain the suitable interfaces for the reaction, was also performed as a control experiment. No formation of propanal was observed.

Hydroformylation with in situ decomposition of MeOH over the tandem $CeO_2$—$Pt$—$SiO_2$ catalyst gave a TOF for propanal of $2.6 \times 10^{-2}$ $s^{-1}$ per Pt atom, which was much faster than that obtained for ethylene hydroformylation with CO and $H_2$ gas over the $Pt$—$SiO_2$ catalyst. Two reasons for the better performance of the tandem catalyst are proposed here. First, for the in situ tandem catalytic reaction, MeOH decomposition occurred preferentially at the $Pt$—$CeO_2$ interface while the rate of MeOH formation by CO hydrogenation is significantly decreased because of the high MeOH concentration. The high density of CO and hydrogen at the Pt surface is also beneficial for ethylene hydroformylation. Secondly, it is also possible that the electronic effects of $CeO_2$ contribute to fundamentally change the catalytic properties of the $Pt$—$SiO_2$ interface for more efficient hydroformylation.

Figure 11:
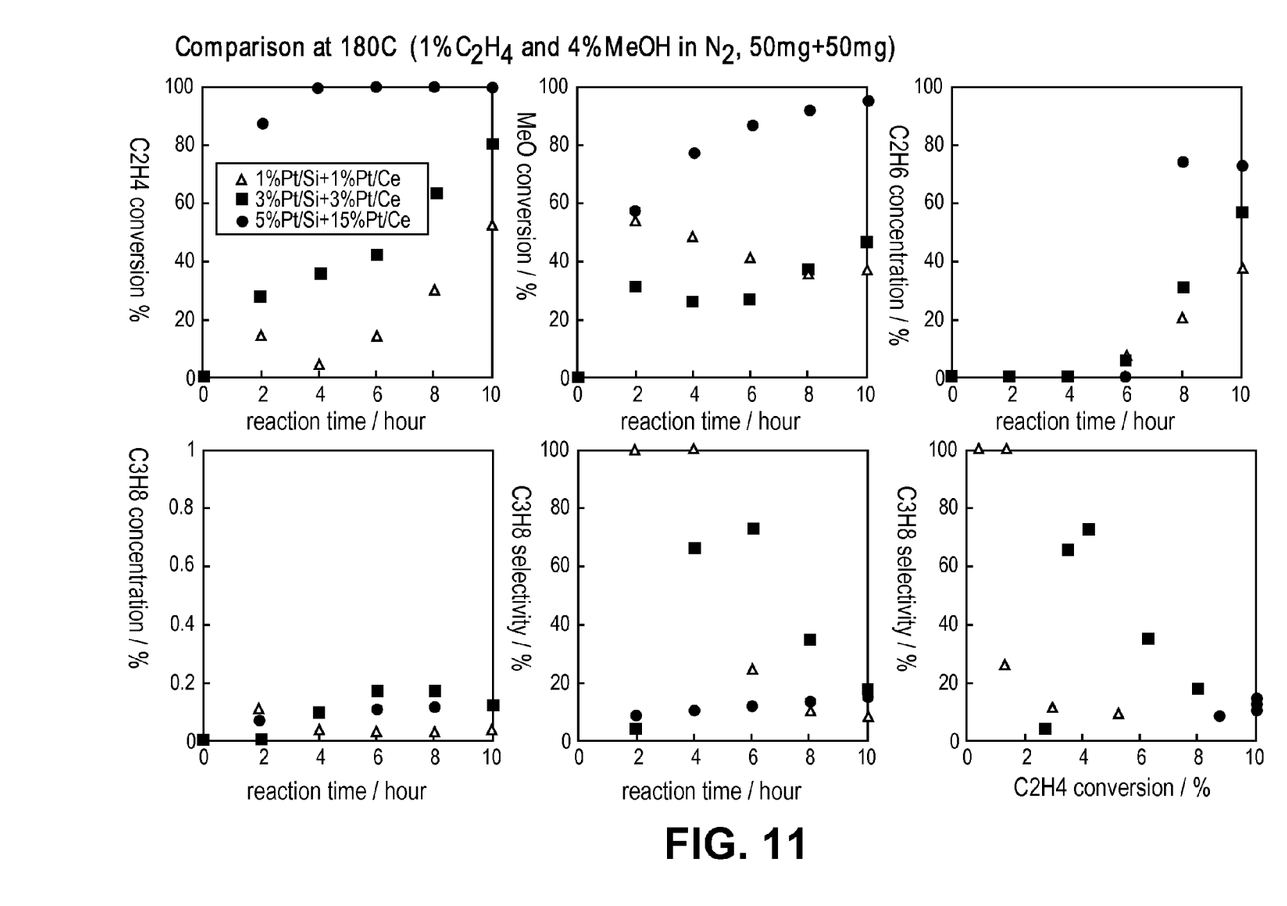
FIG. 11 illustrates time courses of ethylene and MeOH conversions and ethane and propane concentrations in an effluent over the mixture of Pt/$SiO_2$ and Pt/$CeO_2$ in a cyclic reactor.
Figure 12A:
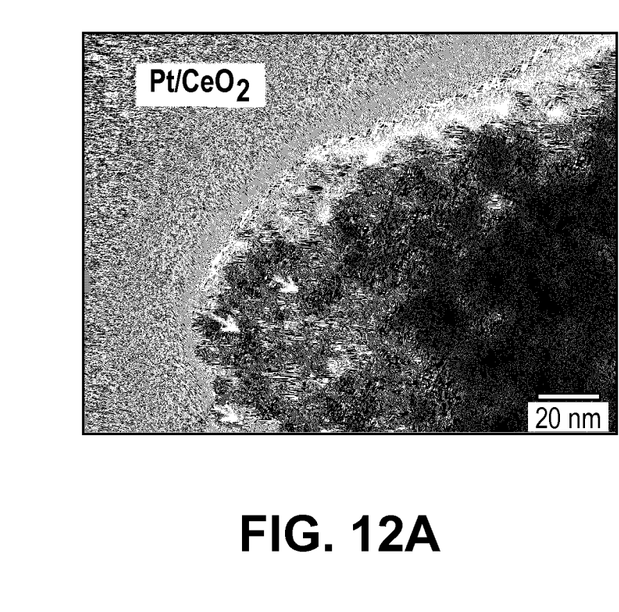
FIG. 12 illustrates TEM images of 15%Pt/$CeO_2$ and of 10% Pt/$SiO_2$.
Figure 12B:
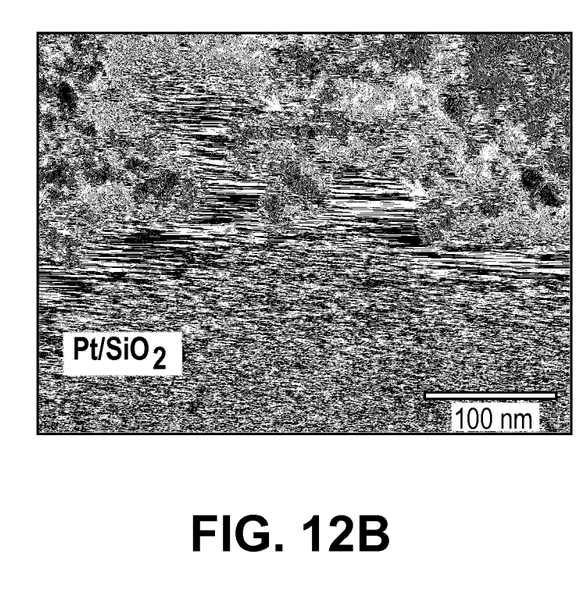

In order to demonstrate the unique properties of our tandem catalysts, the same catalytic reactions were also examined over physical mixtures of $Pt/CeO_2$ and $Pt/SiO_2$ prepared by a conventional impregnation method. The Pt concentration was changed from 1 to 5 wt % for both catalysts. These physical mixture catalysts always produced ethane as a primary product and small amount of propane, which is likely to be formed by the successive hydrogenation of propanal (see FIG. 11). At the mixture of 3% $Pt/SiO_2$ and 3% $Pt/CeO_2$, the TOF of propane formation was $5.7 \times 10^{-4}$ $s^{-1}$ per Pt atom, which is much slower than the TOF of propanal formation, $2.6 \times 10^{-2}$ $s^{-1}$ per Pt atom, over the tandem catalyst. The different catalytic behaviors between the tandem catalyst and mixture catalysts clearly demonstrated the designed interfaces in our tandem catalysts can be used to program sequential chemical reactions effectively. FIG. 12 illustrates TEM images of 15% $Pt/CeO_2$ and of 10% $Pt/SiO_2$.

The novel concept of a nanocrystal bilayer "tandem catalyst" involves multiple distinct metal-metal oxide interfaces corresponding to specific catalytic activities and selectivities. This concept was tested using a $CeO_2/Pt$ nanocube bilayer structure with well-defined surface structures on a silica substrate. Ethylene hydroformylation with hydrogen and carbon monoxide formed in situ by MeOH decomposition was demonstrated. Sequential chemical reactions at two different neighboring metal-metal oxide interfaces acted to selectively produce propanal. While tandem catalysis has been previously employed in homogenous catalytic systems,[24,25] the current invention represents the first such attempt using rationally designed and assembled nanocrystal bilayers with multiple built-in metal-metal oxide interfaces. This new concept of nanocrystal tandem catalysis represents a powerful approach towards designing high performance, multi-functional nanostructured catalysts.

Methods

Platinum and Ceria Nanocubes Synthesis.

Platinum nanocubes and ceria nanocubes were prepared by reported methods with minor modifications.[18,19]

An aqueous solution of $K_2PtCl_4$ (10 mM, 1 mL) was added to an aqueous solution of trimethyltetradecylammonium bromide (TTAB, 119 mM, 8.4 mL). After vigorous stirring, the solution was left at room temperature until a white crystalline solid formed. Then the mixture was heated at 50° C. with magnetic stirring until a clear solution was achieved. To the solution was added an ice cold aqueous solution of $NaBH_4$ (500 mM, 0.6 mL). Excess hydrogen formed during the first 15 min was released through a needle. The solution was stirred for more than 6 hours. The crude product was purified by discarding the precipitate following centrifugation at 3000 rpm for 30 min. The procedure was repeated four times. The shape of particles was observed by a Tecnai 12 Transmission electron microscope or Tecnai G2 S-Twin.

Oleylamine coated Pt nanocubes were obtained by performing ligand exchange on the purified Pt nanocubes described above. Platinum nanocubes capped with TTAB were collected by centrifugation at 14,000 rpm for 30 min. The resulting powder ($1.8 \times 10^{-5}$ mol Pt, nominal) was then washed with deionized water twice and re-dispersed in water and oleylamine (61 μmol, 20 μL). The suspension was heated at 50° C. overnight with magnetic stirring. The slurry was then washed with methanol and a chloroform methanol mixture several times before re-dispersing the particles in $CHCl_3$.

Cerium oxide nanocubes were prepared by autoclave at high temperature.[19] Hydrochloric acid (50 μL), toluene (15 mL), oleic acid (1.5 mL) and tert-butylamine (0.15 mL) were added to an aqueous solution of cerium nitrate hexahydrate (16.7 mM, 15 mL) in a Teflon cup (45 mL inner volume). The Teflon cup was sealed in a stainless steel jacket and heated to 180° C. for 24 hours. The organic phase was collected and purified by centrifugation at 3000 rpm for 5 min. The particles were precipitated by addition of double the volume of ethanol, followed by centrifugation at 14,000 rpm for 10 min to isolate the yellowish white powder. The powder was washed twice with a hexane-ethanol mixture.

LB Film Preparation.

Platinum LB films were prepared with oleylamine-capped Pt nanocubes. Following ligand exchange and washing, the Pt-oleylamine particles were re-dispersed in chloroform (0.5 mL). The solution was slowly dropped onto a water subphase on a LB trough. After evaporation of the chloroform over 30 min, the film was compressed until a surface pressure of 10-15 mN/m was achieved. The resulting film was aged for 30 min and then transferred onto a Si substrate. Ceria nanocube LB films were prepared as the same manner with a chloroform solution of ceria nanocubes. HRTEM images and EDX spectra were recorded on a Philips CM200.

Catalysis Measurements.

All catalysis measurements were carried out with a closed circulation set up. A Si wafer loaded with the nanocube bilayer film was loaded into a glass tube with an inner diameter of 11 mm. A stream of $N_2$ gas was passed over the sample, which was then heated to the desired temperature for measurement. The temperature was monitored with a thermocouple inserted into a glass sheath placed onto the sample. After the temperature stabilized, the reaction gas of 40 torr CO, 100 torr $O_2$ and 620 torr $N_2$ was introduced into the reaction chamber to examine CO oxidation catalysis. The reaction products were quantified approximately every 30 min by a gas chromatograph with two columns and TCD detectors. A Molecular Sieve 5A column with Ar carrier gas was used for quantification of $O_2$, $N_2$ and CO, and a Poraplot Q column with He carrier gas was used for $CO_2$ quantification. The number of Pt atoms exposed to the reaction gas was estimated from SEM images. The MeOH decomposition reaction was carried out in a similar manner. $N_2$ gas with 30 torr MeOH was introduced into the reaction chamber with the catalyst. $H_2$ produced by the catalytic reaction was separated and quantified by the Molecular Sieve 5A column. Hydroformylation was performed with a gas mixture of 7.6 torr ethylene, 30 torr CO, 30 torr $H_2$ and 692 torr $N_2$. Product analysis was performed every 2 hours. Propanal formed during the reaction was separated and quantified with a Poraplot Q column. Ethylene hydroformylation with $H_2$ and CO formed in situ by methanol decomposition was investigated with a gas mixture of 7.6 torr ethylene, 30 torr MeOH and 722 torr $N_2$.

It is to be understood that the above description and examples are intended to be illustrative and not restrictive. Many embodiments will be apparent to those of skill in the art upon reading the above description and examples. The scope of the invention should, therefore, be determined not with reference to the above description and examples, but should instead be determined with reference to the appended claims, along with the fill scope of equivalents to which such claims are entitled. The disclosures of all articles and references, including patent applications and publications, are incorporated herein by reference for all purposes.

REFERENCES

[1] Centi, G. & Perathoner, S. Catalysis: Role and Challenges for a Sustainable Energy. Top. Catal. 52, 948-961 (2009).

[2] Norskov, J. K., Bligaard, T., Rossmeisl, J. & Christensen, C. H. Towards the Computational Design of Solid Catalysts. Nat. Chem., 1, 37-46 (2009).

[3] Ott, L. S. & Finke, R. G. Transition-metal Nanocluster Stabilization for Catalysis: A Critical Review of Ranking Methods and Putative Stabilizers, Coord. Chem. Rev. 251, 1075-1100 (2007).

[4] Somorjai, G. A., Frei, H. & Park, J. Y. Advancing the Frontiers in Nanocatalysis, Biointerfaces, and Renewable Energy Conversion by Innovations of Surface Techniques. J. Am. Chem. Soc. 131, 16589-16605 (2009).

[5] Somorjai, G. A., Tao, F, & Park, J. Y. The Nanoscience Revolution: Merging of Colloid Science, Catalysis and Nanoelectronics. Top. Catal, 47, 1-14 (2008).

[6] Si, R. & Flytzani-Stephanopoulos, M. Shape and Crystal-plane Effects of Nanoscale Ceria on the Activity of Au—$CeO_2$ Catalysts for the Water-gas Shift Reaction. Angew. Chem. Int. Ed. 47, 2884-2887 (2008).

[7] Xie, X. W., Li, Y., Liu, Z. Q., Hiaruta, M. & Shen, W. J. Low-temperature Oxidation of CO Catalysed by $Co_3O_4$ Nanorods. Nature 458, 746-749 (2009).

[8] Stakheev, A. Y. & Kustov, L. M. Effects of the Support on the Morphology and Electronic Properties of Supported Metal Clusters: Modern Concepts and Progress in 1990s. Appl. Catal., A 188, 3-35 (1999).

[9] Jackson, S. D. et al. Supported Metal Catalysts: Preparation, Characterization, and Function 0.5. Activities and Selectivities of Platinum Catalysts in the Reactions of Cyclopropane, Ethene, 1,3-Butadiene, and 2-Butyne with Dihydrogen. J. Catal. 162, 10-19 (1996).

[10] Jackson, S. D., Kelly, G. J. & Webb, G. Supported Metal Catalysts; Preparation, Characterisation, and Function—Part VI. Hydrogenolysis of Ethane, Propane, n-Butane and iso-Butane over Supported Platinum Catalysts. J. Catal. 176, 225-234 (1998).

[11] Zhou, Z., Kooi, S., Flytzani-Stephanopoulos, M. & Saltsburg, H. The Role of the Interface in CO Oxidation on Au/$CeO_2$ Multi-Layer Nanotowers, Adv, Funct. Mater. 18, 2801-2807 (2008).

[12] Shevchenko, E. V., Talapin, D. V., Kotov, N. A., O'Brien, S. & Murray, C. B. Structural Diversity in Binary Nanoparticle Superlattices. Nature 439, 55-59 (2006).

[13] Urban, J. J., Talapin, D. V., Shevchenko, E. V., Kagan, C. R. & Murray, C. B. Synergism in Binary Nanocrystal Superlattices Leads to Enhanced p-Type Conductivity in Self-assembled PbTe/$Ag_2$Te Thin Films. Nat. Mater. 6, 115-121 (2007).

[14] Ungvary, F. Hydroformylation—Homogeneous in Encyclopedia of Catalysis Vol. 3 (ed Istvan T. Horvath) (John Wiley & Sons, Inc., 2003).

[15] Croy, J. R. et al. Support Dependence of MeOH Decomposition over Size-selected Pt Nanoparticles. Catal. Lett. 119, 209-216 (2007).

[16] Imamura, S. et al. Decomposition of Methanol on Pt-loaded Ceria. Catal. Today 50, 369-380 (1999).

[17] Naito, S. & M., T. Effect of Sodium Cation Addition on the Hydroformylation of Propane over Silica-supported Group VIII Metal Catalysts. J. Chem. Soc. Chem. Commun., 1403-1404 (1989).

[18] Lee, H. et al. Morphological Control of Catalytically Active Platinum Nanocrystals. Angew. Chem. Int. Ed. 45, 7824-7828 (2006).

[19] Yang, S. & Gao, L. Controlled Synthesis and Self-Assembly of $CeO_2$ Nanocubes. J. Am. Chem. Soc. 128, 9330-9331 (2006).

[20] Aliaga, C. et al. Sum Frequency Generation and Catalytic Reaction Studies of the Removal of Organic Capping Agents from Pt Nanoparticles by UV-Ozone Treatment, J. Phys. Chem., C 113, 6150-6155 (2009).
[21] Contreras, A. M., Yan, X.-M., Kwon, S., Bokor, J. & Somorjai, G. A, Catalytic CO Oxidation Reaction Studies on Lithographically Fabricated Platinum Nanowire Arrays with Different Oxide Supports. Catal. Lett. 111, 5-13 (2006).
[22] Kweskin, S. J. et al. Carbon Monoxide Adsorption and Oxidation on Monolayer Films of Cubic Platinum Nanoparticles Investigated by Infrared-visible Sum Frequency Generation Vibrational Spectroscopy. J. Phys. Chem. B 110, 15920-15925 (2006).
[23] Panagiotopoulou, P. & Kondarides, D. I. A Comparative Study of the Water-gas Shift Activity of Pt Catalysts Supported on Single (MOx) and Composite (MOx/$Al_2O_3$, MOx/$TiO_2$) Metal Oxide Carriers. Catal. Today 127, 319-329 (2007).
[24] Wasilke, J. C. et al. Concurrent Tandem Catalysis. Chem. Rev. 105, 1001-1020 (2005).
[25] Felpin, F. X. & Fouquet, E. Heterogeneous Multifunctional Catalysts for Tandem Processes: An Approach toward Sustainability. Chem. Sus. Chem. 1, 718-724 (2008).

What is claimed is:

1. A tandem catalyst comprising:
   a metal nanocrystal, the metal nanocrystal comprising a cubic-shaped nanocrystal;
   a first metal oxide disposed on a first surface of the metal nanocrystal; and
   a second metal oxide disposed on a second surface of the metal nanocrystal,
   wherein the second metal oxide comprises a different metal oxide than the first metal oxide.

2. The tandem catalyst of claim 1, wherein the metal nanocrystal comprises platinum (Pt), wherein the first metal oxide comprises cerium oxide ($CeO_2$), and wherein the second metal oxide comprises silicon dioxide ($SiO_2$).

3. The tandem catalyst of claim 2, wherein an interface between the metal nanocrystal and the cerium oxide is configured to catalyze decomposition of methanol to carbon monoxide and hydrogen.

4. The tandem catalyst of claim 2, wherein an interface between the metal nanocrystal and the silicon dioxide is configured to catalyze ethylene hydroformylation using carbon monoxide and hydrogen to generate propanal.

5. The tandem catalyst of claim 1, wherein the metal nanocrystal has dimensions of less than 10 nanometers.

6. The tandem catalyst of claim 1, wherein the metal nanocrystal has dimensions of 6 nanometers to 8 nanometers.

7. The tandem catalyst of claim 1, wherein the first metal oxide disposed on the first surface of the metal nanocrystal comprises a nanocrystal of the first metal oxide.

8. The tandem catalyst of claim 1, wherein the first metal oxide disposed on the first surface of the metal nanocrystal comprises a nanocrystal of the first metal oxide, and wherein the nanocrystal of the first metal oxide comprises a cubic-shaped nanocrystal.

9. The tandem catalyst of claim 1, wherein the second metal oxide disposed on the second surface of the metal nanocrystal comprises a substrate of the second metal oxide.

10. A method of forming a tandem catalyst, according to claim 1, comprising at least two metal-metal oxide interfaces for the catalysis of sequential reactions comprising:
    depositing a Pt monolayer on a $SiO_2$ substrate; and
    depositing a $CeO_2$ monolayer on the Pt monolayer.

11. A method of claim 10, wherein the two metal-metal oxide interfaces comprise $CeO_2$—Pt and Pt—$SiO_2$.

12. A method of claim 11, wherein the two metal-metal oxide interfaces comprise a nanocrystal bilayer further comprising a $CeO_2$ nanocube monolayer in communication with a Pt nanocube monolayer on the $SiO_2$ substrate.

13. A method of claim 12, wherein the Pt nanocube monolayer is prepared by a Langmuir-Blodgett (LB) method.

14. A method of claim 12, wherein the $CeO_2$ nanocube monolayer film is prepared by drop casting or a Langmuir-Blodgett (LB) method.

* * * * *